(12) United States Patent
Denissen et al.

(10) Patent No.: US 11,083,526 B2
(45) Date of Patent: Aug. 10, 2021

(54) MEDICAL SYSTEM, APPARATUS AND METHOD FOR SHAPE SENSING

(71) Applicant: KONINKLIJKE PHILIPS N.V., Eindhoven (NL)

(72) Inventors: Sander Hans Denissen, Best (NL); Laurent Verard, Katonah, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 614 days.

(21) Appl. No.: 15/549,525

(22) PCT Filed: Feb. 1, 2016

(86) PCT No.: PCT/EP2016/052014
§ 371 (c)(1),
(2) Date: Aug. 8, 2017

(87) PCT Pub. No.: WO2016/131367
PCT Pub. Date: Aug. 25, 2016

(65) Prior Publication Data
US 2018/0014889 A1 Jan. 18, 2018

Related U.S. Application Data

(60) Provisional application No. 62/118,730, filed on Feb. 20, 2015.

(30) Foreign Application Priority Data

Mar. 26, 2015 (EP) .................................... 15161056

(51) Int. Cl.
*A61B 34/20* (2016.01)
*A61B 90/00* (2016.01)

(52) U.S. Cl.
CPC ............ *A61B 34/20* (2016.02); *A61B 90/361* (2016.02); *A61B 2034/2048* (2016.02);
(Continued)

(58) Field of Classification Search
None
See application file for complete search history.

(56) References Cited

U.S. PATENT DOCUMENTS 8,183,520 B2 5/2012 Prisco
9,430,717 B2 8/2016 Denissen
(Continued)

FOREIGN PATENT DOCUMENTS

JP 2007007041 A 1/2007

*Primary Examiner* — Angela M Hoffa
*Assistant Examiner* — Younhee Choi

(57) ABSTRACT

A medical system for shape sensing by interacting with a shape sensing element (12) configured to perform a shape sensing measurement of an interventional device (14) and by interacting with an image data generation unit (28) for generating image data (21) is provided. The medical system includes a shape sensing console (16) in communication with the shape sensing element (12) for generating measurement signals of the shape sensing measurement, a shape reconstruction unit (18) in communication with the shape sensing console for reconstructing a shape (19) of the shape sensing element based on the generated measurement signals, a receiving unit (22) for receiving a position and/or orientation of an apparatus (26, 26') including the image data generation unit (28), a coordinate transformation unit (20) for registering the reconstructed shape (19) by representing the reconstructed shape (19) in a coordinate system based on the received orientation of the apparatus (26, 26'), and a connector unit (32) for connecting the shape sensing console (16) and/or said shape reconstruction unit (18) to the shape (Continued)

sensing element (12), the connector unit (32) being detachably connectable to a housing (30) of the apparatus (26, 26').

14 Claims, 2 Drawing Sheets

(52) U.S. Cl.
CPC ............ *A61B 2034/2051* (2016.02); *A61B 2034/2061* (2016.02); *A61B 2034/2065* (2016.02); *A61B 2090/365* (2016.02); *A61B 2090/372* (2016.02)

(56) References Cited

U.S. PATENT DOCUMENTS

| | | | |
|---|---|---|---|
| 9,625,516 | B2 | 4/2017 | Hopf et al. |
| 2004/0106081 | A1* | 6/2004 | Karazivan ............ A61B 5/0088 433/29 |
| 2013/0109957 | A1* | 5/2013 | 'T Hooft ............ A61B 1/00082 600/424 |
| 2013/0223702 | A1* | 8/2013 | Holsing .................. G06T 1/00 382/128 |
| 2013/0317356 | A1 | 11/2013 | Ramachandran et al. |
| 2013/0324833 | A1 | 12/2013 | Barley et al. |
| 2014/0039306 | A1 | 2/2014 | Klinder et al. |
| 2014/0081659 | A1* | 3/2014 | Nawana ................ A61B 5/1118 705/3 |
| 2014/0303423 | A1 | 10/2014 | Amthor et al. |
| 2014/0309495 | A1* | 10/2014 | Kirma .................... A61B 1/053 600/109 |
| 2015/0018622 | A1* | 1/2015 | Tesar .................... A61B 90/20 600/202 |
| 2015/0126864 | A1 | 5/2015 | Buclow et al. |
| 2015/0282734 | A1* | 10/2015 | Schweikert .......... A61B 5/0006 600/424 |

\* cited by examiner

MEDICAL SYSTEM, APPARATUS AND METHOD FOR SHAPE SENSING

CROSS-REFERENCE TO PRIOR APPLICATIONS

This application is the U.S. National Phase application under 35 U.S.C. § 371 of International Application Serial No. PCT/EP2016/052014, filed on Feb. 1, 2016, which claims the benefit of U.S. Application Ser. No. 62/118,730, filed on Feb. 20, 2015 and European Patent Application No. 15161056.5, filed on Mar. 26, 2015. These applications are hereby incorporated by reference herein.

FIELD OF THE INVENTION

The present invention relates to a medical system, an apparatus and a method for performing shape sensing. It finds application in image-guided interventions and therapeutic procedures. In particular, it finds application in optical shape sensing using elongated medical devices such as endoscopes, catheters and guide wires.

BACKGROUND OF THE INVENTION

In interventional therapies, minimally invasive image-guided procedures are used to diagnose and treat diseases in an organ system. For this purpose, interventional devices with an elongated part insertable into the body of a living being, such as a human, are applied. In this way, it is possible to diagnose and treat patients using the least invasive techniques so that the risk of complications is minimized and the health outcomes are improved.

In interventional therapeutic procedures, it is essential to accurately locate the interventional device within the patient's body. In particular, it is essential to determine and adjust the position and/or orientation of the interventional device in order to achieve the desired therapeutic result. In this regard, different types of shape sensing elements are known in the art for performing a shape sensing measurement of interventional devices.

For instance, the shape sensing element may comprise a fluoroscopy marker tracking element configured to be used in interventional procedures typically performed under X-ray fluoroscopy guidance that gives the interventionalist information about the anatomy and function of the treated body part. The shape sensing element may alternatively comprise an electromagnetic (EM) localization element comprising one or more EM sensors, wherein the EM sensors are used to localize points at intervals along the interventional device.

The shape sensing element may comprise an optical shape sensing element, such as an optical fiber comprising one or more cores, wherein the optical fiber has an elongated portion insertable into the interventional device. Such a shape sensing technique is generally known as "optical shape sensing" (OSS) and provides a means to measure the shape of an interventional device by tracking the location and shape of the optical fiber inserted into the interventional device.

The optical fiber may be integrated into a hollow space inside the interventional device, or physically attached to the device. Optical shape sensing does not use hazardous substances or radiation and is free from external interference such as electromagnetic fields or radiations. Therefore, it is compatible to nearly any clinical setting.

The medical systems known in the art for performing shape sensing in interventional therapeutic procedures have the drawback that the shape sensing measurement cannot be carried out with sufficient accuracy, leading to a high percentage of erroneous positioning or mal-positioning of interventional devices.

For instance, about 10 million treatments are performed in the US per year using Central Venous Catheters (CVC) and Peripherally Inserted Central Catheter (PICC) to support critically ill patients, in particular those suffering from cancer, post-surgical effects and trauma. The patients are treated with drugs, nutrients, or chemotherapy. A mal-position rate of approximately 25% to 35% of all catheters has been registered. Besides serious complications in the interventional procedures, this causes increased treatment costs and delayed recovery.

Millions of feeding tubes are inserted per year to support clinically ill patients who cannot feed on their own. Gastric function is critical for the patient's survival and maintaining immunity to viruses. Recent studies have revealed that about 2.4% of feeding tubes are mal-positioned causing serious complications. Even if a feeding enteral tube is correctly inserted and the initial gastric placement is confirmed, for instance by X-ray, continuous assessment of the position and/or orientation of the feeding tube is required. Vomiting, coughing, retching, or suctioning of the patient can cause the distal tip of the feeding tube to migrate upward into the esophagus or downward into the duodenum.

Furthermore, it is also possible for a portion of the feeding tube to become coiled in the pharynx. The severity of resulting complications depends on whether the mal-positioned tube has been used to deliver feedings or medication. Possible outcomes include aspiration, pneumothorax, and sepsis.

US 2013/0324833 A1 discloses a medical method and system including a medical imaging system for generating images of an interventional procedure. An overlay generator is configured to generate an overlay image on the images of the interventional procedure. An interventional device tracking system is configured to track a three-dimensional position, orientation and shape of the interventional device during the procedure, wherein the overlay image is dynamically updated in response to deformations caused to an organ of interest by the interventional device during the procedure.

WO2014/053925A1 discloses a system and method for registering a coordinate system for a shape sensing system to a coordinate system for pre-procedural or intra-procedural imaging data.

SUMMARY OF THE INVENTION

It is an object of the present invention to provide a medical system, apparatus and method for shape sensing which enable to reduce mal-positioning of interventional devices and improve localization of the interventional devices in interventional procedures.

In a first aspect of the present invention a medical system is presented for shape sensing by interacting with a shape sensing element configured to perform a shape sensing measurement of an interventional device and by interacting with an image data generation unit for generating image data, the medical system comprising a shape sensing console in communication with the shape sensing element for generating measurement signals of the shape sensing measurement, a shape reconstruction unit in communication with the shape sensing console for reconstructing a shape of the shape sensing element based on the generated measurement signals, a receiving unit for receiving a position and/or orientation of an apparatus comprising the image data generation unit, a coordinate transformation unit for registering the reconstructed shape by representing the reconstructed shape in a coordinate system based on the received orientation of the image data generation unit, and a connector unit for connecting the shape sensing console and/or the shape reconstruction unit to the shape sensing element, the connector unit being detachably connectable to a housing of the apparatus using fixing menas.

In a further aspect of the present invention an apparatus is presented for shape sensing by interacting with a shape sensing element configured to perform a shape sensing measurement of an interventional device, the apparatus comprising an image data generation unit for generating image data, a medical system as claimed herein, wherein the medical system is configured to interact with the image data generation unit and register a reconstructed shape of the shape sensing element by representing the reconstructed shape in a coordinate system based on a received position and/or orientation of the apparatus, and a housing for detachably connecting the medical system and/or the image data generation unit.

In a further aspect of the present invention a method is presented for shape sensing by interacting with a shape sensing element configured to perform a shape sensing measurement of an interventional device and by interacting with an image data generation unit for generating image data, the method comprising the steps of generating measurement signals of the shape sensing measurement, reconstructing a shape (19) of the shape sensing element based on the generated measurement signals, registering the reconstructed shape by representing the reconstructed shape in a coordinate system based on a received position and/or orientation of an apparatus comprising the image data generation unit and connecting the shape sensing console and/or the shape reconstruction unit to the shape sensing element using a connector unit connectable to a housing of the apparatus using fixing means.

Preferred embodiments of the invention are defined in the dependent claims. It shall be understood that the claimed apparatus and method have similar and/or identical preferred embodiments as the claimed system and as defined in the dependent claims.

A shape sensing measurement can be carried out for the interventional device by the shape sensing element, which is connected to, in particular at least partially inserted into the interventional device. The goal of the shape sensing measurement is to obtain the shape of the interventional device so as to determine its localization, in particular position and/or orientation within a body part of a patient under treatment. For this purpose, the shape sensing console generates measurement signals from the shape sensing measurement. Based on the measurement signals, the shape construction unit can then reconstruct a shape, in particular a three-dimensional shape, of the shape sensing element.

The orientation of the apparatus, preferably a mobile apparatus, may be derived from other data such as image data obtained by an image capture unit, data from an orientation tracking unit and/or a position orientation tracking unit. Other data including motion data obtained from a hinge setting from a hinged display and/or from a swivel or pendulum, gyroscope data and/or accelerometer data can also be used to derive the orientation of the apparatus. Preferably, the determined orientation data comprise 3D and/or 6D coordinate data. In particular, the orientation data may be derived from real-time data/live feed, such as real-time image data/live image feed, real-time camera data/ live camera feed, real-time gyroscope data/live gyroscope feed and/or real-time accelerometer data/live accelerometer feed.

Advantageously, the medical device according to the present invention is detachably connectable to the housing of an external apparatus, wherein the apparatus may comprise a stationary apparatus such as a personal computer, or a mobile apparatus such as a tablet computer or a smartphone. In this way, the medical device enables to process shape sensing measurement data on a mobile basis, thereby utilizing the mobile communication network to acquire and exchange shape sensing data. This leads to higher efficiency and practicability of performing shape sensing for a large number of users possessing a mobile apparatus or a stationary apparatus.

Moreover, the reconstructed shape can be registered based on the received position and/or orientation of the apparatus. In particular, when the received position and/or orientation of the apparatus is correlated to or derived from the generated image data, this enables overlaying of the reconstructed shape onto the generated image data. A new dataset comprising both the originally generated data and the reconstructed shape is thus obtained. Advantageously, this facilitates the presentation, processing, exchanging and/or modification of the reconstructed shape of the shape sensing element and/or the interventional device, leading to increased efficiency and accuracy of the shape sensing procedure. The localization of the interventional device is improved and the mal-positioning of the interventional device reduced. Hence, the present invention fulfills the afore-mentioned object completely.

This shape sensing element may be integrated in the interventional device, such as a catheter. The interventional device, including the shape sensing element, is a disposable entity that is integrated in the interventional device, e.g. catheter. Hence, the present invention allows for connection to or interaction with the shape sensing element without including it. This holds for all different tracking modalities, in particular OSS tracking, EM tracking and fluoroscopy tracking. In the case of OSS tracking, an optical fiber is integrated in the interventional device. In the case of EM tracking, coils are integrated in the interventional device. In the fluoroscopy case, the markers are provided on the interventional device.

In a preferable embodiment, the coordinate transformation unit is configured to register the reconstructed shape with the image data generated by the image data generation unit. In this way, the reconstructed shape can be overlaid to the generated image data. Since image data are easily available, the present invention advantageously realizes easy registration of reconstructed shape.

In a preferably embodiment, the receiving unit is configured to receive the position and/or orientation of the apparatus determined from the generated image data relative to a subject contained in the image data, and/or from data obtained by a different unit, such as an orientation tracker, a position tracker, a gyroscope, an accelerometer, a hinged display, a swivel and/or a pendulum. In this way, the present invention enables to utilize the position and/or orientation of the apparatus determined from a variety of sources. Advantageously, this increases the reliability of the so-determined position and/or orientation of the image data generation unit, leading to increased accuracy of the registration of reconstructed shape.

Preferably, the coordinate transformation unit is configured to automatically register the reconstructed shape after the receiving unit has received the orientation of the apparatus being facing the subject. In this way, the present invention is able to automatically perform accurate shape registration, thereby increasing the efficiency of shape sensing while maintaining its reliability.

In another preferable embodiment, the coordinate transformation unit is configured to perform a rigid coordinate transformation such as a translational and/or rotational transformation, or a look-at transformation, and/or to determine a correlation function and/or a fit between the reconstructed shape and the generated data. The rigid coordinate transformation is shape-preserving for the reconstructed shape. Hence, details contained in the reconstructed shape can be securely processed during overlaying. Advantageously, this increases the accuracy and reliability of the shape sensing procedure. Further, the features in both the reconstructed shape and the generated data can be analyzed and/or compared, leading to quantitatively improved overlaying of the reconstructed shape onto the generated data. Advantageously, this further improves the accuracy and reliability of the shape sensing procedure.

Preferably, the coordinate transformation unit is configured to determine a fit between the reconstructed shape and a shape of the shape sensing element extracted from the generated data. This enables to correlate the shape, in particular the position and/or orientation of the shape sensing element according to the reconstructed shape to that according to the generated data, in particular image data. Advantageously, the overlaying of the reconstructed shape is facilitated.

Preferably, the coordinate transformation unit is configured to determine an up-vector semi-automatically and/or using user interaction. The up-vector is the direction of an axis in a cross-section or a three-dimensional representation of a body part displayed in a medical image. In this way, the up-vector can be determined with high accuracy. Advantageously, the reconstructed shape can be more easily overlaid onto the generated data.

In another preferable embodiment, the apparatus comprises a mobile apparatus such as a tablet computer and/or a smartphone. In this way, the apparatus is built with high mobility and flexibility. Advantageously, this enables to perform the shape sensing procedure with high mobility and flexibility.

In another preferable embodiment, the image data generation unit is configured to generate real-time image data. Real-time image data may comprise real-time camera data, real-time ultrasonic data and/or real-time thermal data. Advantageously, the overlaying of the reconstructed shape is dynamic, wherein the result of the overlaid shape is constantly updated.

In another preferable embodiment, the image data generation unit comprises an optical camera, an ultrasonic camera and/or a thermal camera. In this way, the apparatus is able to generate various types of data, so that the reconstructed shape can be overlaid onto the various types of data. Advantageously, this extends the possibilities of presenting, processing and/or modifying the reconstructed shape, leading to further improved shape sensing procedure.

In another preferable embodiment, the image data generation unit comprises a plurality of cameras arranged surrounding a plurality of edges of the housing of the apparatus. In this way, the reconstructed shape can be overlaid to image data obtained from various view angles/perspectives. Advantageously, this further increases the accuracy of shape sensing.

In another preferable embodiment, the apparatus further comprises a display unit for displaying a content of the image data generated by the image data generation unit and/or the registered reconstructed shape. This enables the user to view the image data and/or the registered/overlaid reconstructed shape. This facilitates easy adjustment and/or modification of the overlaid reconstructed shape. Advantageously, the shape sensing procedure is more reliable.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
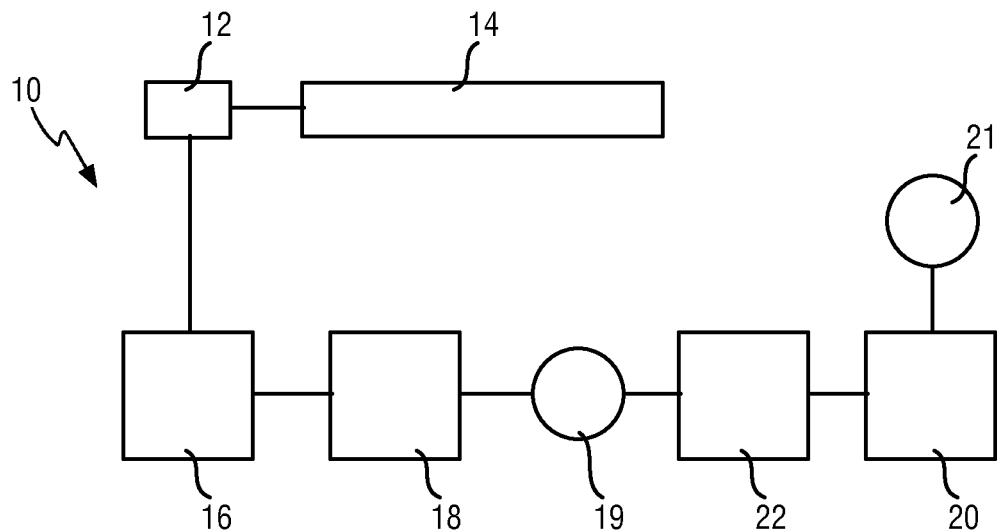
FIG. 1 shows a schematic block diagram of a medical system for shape sensing.

FIG. 1 shows a schematic block diagram of a medical system 10 for shape sensing by interacting with a shape sensing element 12 configured to perform a shape sensing measurement of an interventional device 14 connected with the shape sensing element 12 and by interacting with an image data generation unit 28 (shown in FIGS. 3 and 5) for generating image data 21. The medical system 10 comprises a shape sensing console 16 in communication with the shape sensing element 12 for generating measurement signals of the shape sensing measurement. The medical system 10 also comprises a shape reconstruction unit 18 in communication with the shape sensing console for reconstructing a shape 19 of the shape sensing element based on the generated measurement signals. The medical system 10 comprises a receiving unit 22 for receiving a position and/or orientation of an apparatus comprising the image data generation unit 28 (shown in FIGS. 3 and 5), in particular relative to a subject such as a patient. The medical system 10 further comprises a coordinate transformation unit 20 for registering the reconstructed shape 19, preferably overlaying the reconstructed shape 19 onto the generated image data 21, by representing the reconstructed shape 19 in a coordinate system based on the received position and/or orientation of the apparatus. Finally, the medical system 10 comprises a connector unit 32 for connecting the shape sensing console 16 and/or the shape reconstruction unit 18 to the shape sensing element 12. As will be shown in FIGS. 3 and 5, the connector unit 32 is detachably connectable to a housing 30 of an apparatus 26, 26'.

The shape sensing element 12 may comprise an optical shape sensing element such as an optical fiber comprising one or more cores, as elucidated below with reference to FIG. 2. Alternatively, the shape sensing element 12 may comprise an electromagnetic (EM) tracking element, a fluoroscopy marker tracking element and/or another type of shape sensing element known in the field of shape sensing.

The shape sensing console 16 may comprise an optical interrogator for generating measurement signals being scattering spectrum signals indicative of an amplitude and/or a phase of a scattering in an elongated portion of the shape sensing element 12 comprising an optical fiber, as elucidated below with reference to FIG. 2. Alternatively, the shape sensing console 16 may be configured to generate measurement signals of EM and/or fluoroscopy marker tracking measurement.

The shape construction unit 18 is configured to reconstruct a shape of the shape sensing element 12, in particular an elongated portion of an optical fiber inserted into the interventional device 14. Preferably, the shape construction unit 18 is configured to perform a three-dimensional shape reconstruction based on scattering spectrum signals, in particular reflection spectrum signals. Alternatively, the shape construction unit 18 is configured to perform a three-dimensional shape reconstruction based on EM tracking signals and/or fluoroscopy marker tracking signals.

The receiving unit 22 and/or the coordinate transformation unit 20 may comprise a central processing unit (CPU), a manual data processing unit, an automatic data processing unit, and/or an electronic data processing unit. The receiving unit 22 and the coordinate transformation unit 20 may preferably be integrated into one single unit.

Preferably, the receiving unit 22 is configured to receive the position and/or orientation of the apparatus determined from the generated image data 21 relative to a subject contained in the image data 21, relative to which the position and/or orientation is determined, and/or from data obtained by a different unit, such as an orientation tracker, a position tracker, a gyroscope, an accelerometer, a hinged display, a swivel and/or a pendulum.

Further preferably, the coordinate transformation unit 20 is configured to automatically register the reconstructed shape 19 after the receiving unit 22 has received the orientation of the apparatus facing the subject.

Besides overlaying of the reconstructed shape 19 onto the generated image data 21 by means of registration, the coordinate transformation unit 20 may preferably be configured to perform a data conversion from one data format to another data format, data validation to ensure the correctness of the generated data 21, data sorting to arrange items of the generated data 21 in one or more sequences and/or in one or more sets, data summarization to extract one or more main aspects of the generated data 21, data aggregation to combine multiple sets of data and/or data analysis to collect, organize, analyze, interpret and/or present the generated data 21.

After overlaying, a new data set comprising both the originally generated image data 21 and the reconstructed shape 19 is thus obtained. Advantageously, both the reconstructed shape 19 and the content of the generated image data 21 can be presented using a single data set. This facilitates the presentation of the reconstructed shape 19 of the shape sensing element 12. Further, the reconstructed shape 19 of the shape sensing element 12 can be more easily processed, exchanged and/or modified leading to increased efficiency and accuracy of the shape sensing.

A shape sensing measurement can be carried out for the interventional device using the medical system 10. The shape sensing element 12 is at least partially inserted into the interventional device 14. The goal of the shape sensing measurement is to obtain the shape of the interventional device 14 so as to determine its localization, in particular position and/or orientation within the body part under treatment. For this purpose, the shape sensing console 16 generates measurement signals from the shape sensing measurement. Based on the measurement signals, the shape construction unit 18 can then reconstruct a shape, in particular a three-dimensional shape, of the shape sensing element 12. The shape of the interventional device 14 can be indirectly obtained in this way.

The generated data 21 can be processed by the coordinate transformation unit 20, which is also configured to process data regarding the reconstructed shape of the shape sensing element 12 and/or the interventional device 14.

The coordinate transformation unit 20 is configured to represent the reconstructed shape 19 in a reference frame of the generated image data 21. The reference frame is in particular a coordinate system, for instance a coordinate system of one or more images contained in the generated image data. In this way, the present invention enables to represent the reconstructed shape 19 of the shape sensing element 12 in the same reference frame as the content of the generated data, in particular the image contained in the generated image data. Advantageously, this further facilitates the processing, exchange and/or modification of the reconstructed shape 19, leading to further improved shape sensing.

Figure 2:
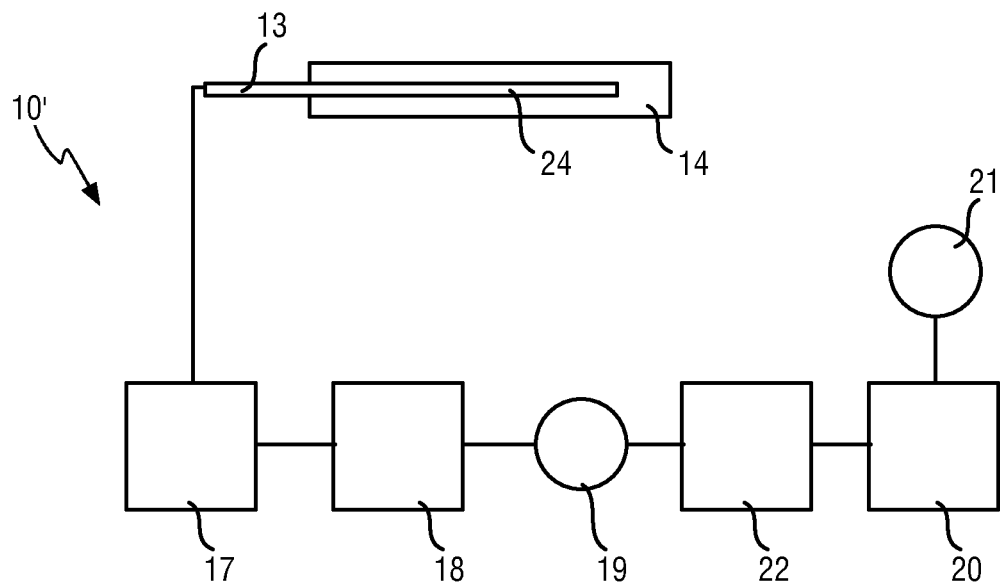
FIG. 2 shows a schematic block diagram of another medical system for optical shape sensing.

FIG. 2 shows another medical system 10' comprising essentially the same components as in FIG. 1, wherein the shape sensing element 12 comprises an optical fiber 13, the optical fiber having an elongated portion 24 insertable into the interventional device 14. The optical fiber 13 may comprise single or multiple cores, wherein each of the multiple cores is configured to perform an optical shape sensing (OSS) measurement separately from other cores.

The optical fiber 13 is configured to guide a light signal generated by a light source, for instance a tunable laser source (TLS), along the elongated portion 24 within the device 14, wherein the light signal undergoes a scattering, in particular a reflection, at a point of the elongated portion 24 and is subsequently guided to the shape sensing console 16. Preferably, the optical fiber 13 comprises one or more embedded periodical structures, e.g. fiber Bragg gratings (FBG) and/or non-periodic structures. In this way, Bragg reflection and/or Rayleigh scattering spectrum signals can be investigated leading to high accuracy of the optical shape sensing.

The shape sensing console 16 comprises preferably an interrogator unit 17 for generating scattering spectrum signals, in particular reflection spectrum signals, indicative of an amplitude and/or a phase of a scattering in the elongated portion 24 of the optical fiber 13. Local strain data of the optical fiber 13 can be derived from the scattering spectrum signals, wherein local curvature and/or torsion angle of the optical fiber 13 can be obtained from the local string data. The shape reconstruction unit 18 is preferably configured to determine a three-dimensional shape of the elongated portion 24 of the optical fiber 13. In this way, the position and/or orientation of the interventional device 14 can be determined reliably.

Figure 3:
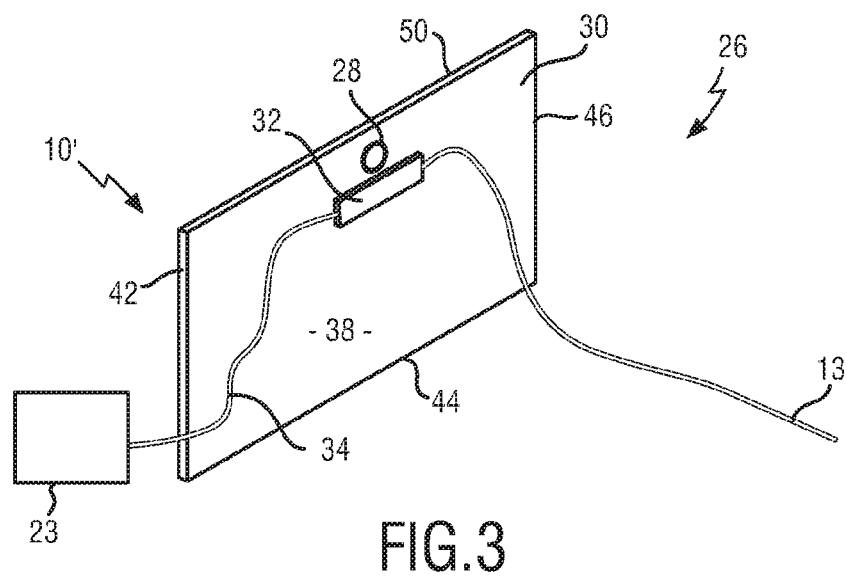
FIG. 3 shows an illustrative diagram of an apparatus for optical shape sensing.

FIG. 3 shows an illustrative diagram of an apparatus 26 comprising an image data generation unit 28 for generating image data. The image data generation unit 28 is preferably an optical camera, an ultrasonic camera or a thermal/infrared camera, wherein the image data generation unit 28 is configured to generate image data containing one or more images.

The apparatus 26 comprises a medical system, in particular the medical system 10, 10' shown in FIGS. 1-2. Preferably, the coordinate transformation unit 20 (shown in FIG. 1-2) is configured to overlay the reconstructed shape 19 of the interventional device 14 and/or the shape sensing element 12, in particular the optical fiber 13, onto the image data generated by the image data generation unit 28.

Preferably, the shape sensing console 16, in particular the interrogator unit 17, the shape reconstruction unit 18, the receiving unit 22 and/or the coordinate transformation unit 20 are configured as one single unit 23. The apparatus 26 further comprises a connector unit 32 and a housing 30 for detachably connecting and/or accommodating the image data generation unit 28 and/or the medical system 10'. In particular, the housing 30 is preferably a tablet computer housing comprising a front side 36 and a back side 38.

Preferably, the apparatus 26 comprises or interacts with a determination unit for determining the position and/or orientation of the apparatus 26, in particular a display unit of the apparatus 26. The determination unit may determine the position and/or orientation of the apparatus from the generated image data 21 relative to a subject contained in the image data 21, relative to which the position and/or orientation is determined. Alternatively or additionally, the determination unit may determine the position and/or orientation from data obtained by a different unit, such as an orientation tracker, a position tracker, a gyroscope, an accelerometer, a hinged display, a swivel and/or a pendulum.

Preferably, when the apparatus 26, in particular a mobile apparatus, is turned towards a patient, the determination unit determines the orientation of the apparatus 26 as being facing the patient. In this case, image data of the patient can be shown on the display unit. Further, the reconstructed shape of the interventional device 14 and/or the shape sensing element 12 can be overlaid onto the image of the patient on the basis of the determined orientation of the mobile apparatus 26, in particular the display unit.

FIG. 3 shows a view onto the back side 38 of the housing 30. As can be seen in FIG. 3, the connector element 32 is detachably connectable to the back side 38 of the housing 30 to connect the optical fiber 13 on one hand and the unit 23 via a wiring 34 on the other hand. The wiring 34 comprises preferably one or more optical fibers. The image data generation unit 28 comprises an image capture surface and is preferably an optical camera, wherein the image capture surface is arranged on the back side 38 of the housing 30. As can be seen in FIG. 3, the unit 23 is arranged separately from the housing. Alternatively, the image capture surface of the image capture unit 28 may be arranged on the front side 36 of the housing 30.

Figure 4:
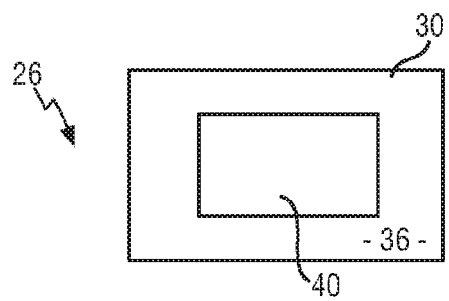
FIG. 4 shows an illustrative diagram of a front view of the apparatus shown in FIG. 3.

FIG. 4 shows a view onto the front side 36 of the apparatus 26 of FIG. 3. A display unit 40 is arranged on the front side 36 of the housing 30, wherein the display unit 40 is configured to display a content of the image data generated by the optical camera 28 and comprises preferably a display field.

Figure 5:
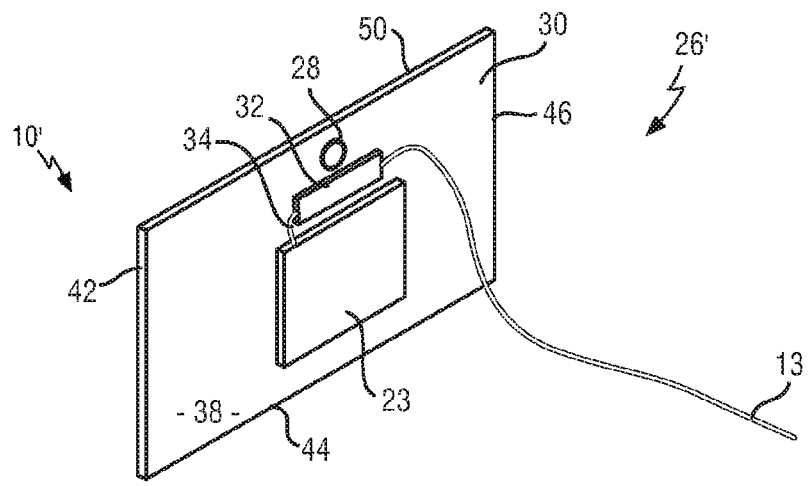
FIG. 5 shows an illustrative diagram of another apparatus for optical shape sensing.

In FIG. 5, a similar apparatus 26' is shown which comprises essentially all the components shown in FIG. 3, except that the unit 23 is arranged not separately from the housing 30 but attached on the back side 38 of the housing 30. It is noted that besides the connector unit 32, the unit 23 is also detachably connected to the back side 38 of the housing 30, thereby forming another connector unit. The connection between the connector unit and the housing 30 may be realized using glue or other fixing means known in the art.

Although the apparatus 26, 26' shown in FIGS. 3-5 is configured to be used in optical shape sensing, it is understood that the apparatus 26, 26' may alternatively comprise one or more medical systems 10 for shape sensing based on other techniques, such as using an ultrasonic, thermal/infrared camera, EM tracking and/or fluoroscopy marker tracking. One or more of the components of the unit 23 is preferably powered by its own power source, such as a battery, and/or a power source of the housing 30.

Preferably, the apparatus 26, 26' comprises a mobile apparatus, such as a tablet computer and/or a Smartphone. The apparatus 26, 26' may be dockable to a docking station so as to enable a stationary apparatus. Preferably, the unit 23 of the apparatus 26, 26' being a tablet computer is configured to carry out one or more tasks by running a tablet software. The tasks preferably include:

- receiving image data via the optical camera 28, wherein the image capture surface of the optical camera 28 may be arranged on the front side 36 or back side 38 of the housing 30;
- receiving medical data via a wireless data connection and/or a wired data connection, the wireless data connection comprising one or more DICOM link and/or one or more proprietary links;
- manipulating registration information and/or image information, the registration information comprising contact information and/or clinical information;
- creating, modifying and/or deleting virtual objects such as landmarks using a user interface displaced by the display unit 40;
- determining absolute orientation using a gyroscope, an internal accelerometer, an orientation tracking unit/sensor, and/or based on the shape sensing; and/or
- acquiring data regarding the reconstructed shape of the shape sensing element 12 wirelessly or via the unit 23 distantly connected or attached to the housing 30.

Preferably, the image data generated by the camera 28 comprise real-time data or live camera feed. The medical data may comprise previously recorded and/or real-time/live medical data including registration information and/or image information. Further preferably, the data regarding the reconstructed shape are real-time shape data/live shape data. Preferably, the afore-mentioned tasks may be superimposed and/or blended by setting one or more user preferences accordingly, wherein the user preferences may be shown by the display unit 40, preferably on the display field. It is understood that the terms "camera feed" and "data feed" refer to data generated by a camera or another entity wherein the generated data are received by an interface. It is also understood that the terms "live camera feed", "live medical data" and "live data feed" refer to data that are generated and/or received on a real-time basis, thus being dynamic data in contrast to static data.

In the following, additional features will be described referring to the apparatus 26, 26' being a tablet computer. However, it is understood that the features described hereinafter are applicable to a stationary/non-mobile apparatus.

The optical fiber 13 can be physically attached to the back side 38 of the tablet computer 26, 26', as shown in FIGS. 3, 5. Alternatively, the optical fiber 13 may be surrounded by a sleeve made of sterile materials, wherein the sleeve is flexible and comprises a portion that can be positioned to face the front side 36 of the housing 30. The tablet computer 26, 26' is configured to overlay the reconstructed shape of the optical fiber 13 or the interventional device, into which an elongated portion of the optical fiber 13 is inserted, onto the live camera feed generated by the optical camera 28. This can be done by applying two transformations: Perspective projection of the optical camera 28 of the tablet computer 26, 26', rigid transformation from the reference frame of the optical fiber 13 to the reference frame of the optical camera 28.

For the purpose of perspective projection, the camera 28 needs to be calibrated, wherein the calibrated camera 28 preferably has a minimum camera aspect ratio and/or a minimum camera field-of-view. Further preferably, the calibration may be a pin-cushion calibration and/or a warping calibration.

The rigid transformation may be a translational and/or rotational transformation and enables to transform from the coordinate system of the reconstructed shape to a coordinate system of the image data generated by the camera 28. In particular, the rigid transformation transforms the position and/or orientation of the optical fiber 13 from the coordinate system of the reconstructed shape to the coordinate system of the camera image.

Preferably, this is obtained by positioning the optical fiber 13 or the interventional device 14, into which the elongated portion 24 of the optical fiber 13 is inserted, in the viewing field of the camera 28, followed by generating a camera image of the so-positioned optical fiber 13, followed by detecting the shape of the optical fiber 13 in the generated camera image. Such a shape is, without loss of generality, called "camera image shape".

Then, the fit and/or a correlation function between the detected camera image shape and the reconstructed shape, in particular the three-dimensional reconstructed shape, of the optical fiber 13 can be determined.

Alternatively, the rigid transformation may be performed by placing a sensing tip or any other identifiable part of the interventional device 14 into a center of the viewing field of the camera 28, wherein the center of the viewing field may be indicated by a cross-hair or other identifying marker, preferably in the center of the display field of the camera 28. Subsequently, a look-at transformation is performed in order to identify a position of the sensed device, wherein the identified position corresponds to a position of the sensed device relative to another part of the interventional device as represented in the reference frame or coordinate system of the reconstructed shape.

Preferably, an up-vector, i.e. the direction of an axis in a cross-section or a three-dimensional representation of a body part, in particular at a given point of the body part, can be determined manually or semi-automatically. The manual determination preferably uses user interaction via a user interface, such as a touch screen of the tablet computer 26, 26'. The semi-automatic determination of the up-vector is performed by applying the look-at transformation to a given point of the body part, where the up-vector is to be determined.

The look-at vector alone cannot be used to determine a three-dimensional transformation. The rotation around the look-at vector of the interventional device 14 with respect to the coordinate system of the camera 28 is still required. This rotation can be represented as a vector and is called the up-vector. The up-vector is defined in the three-dimensional coordinate system of the camera 28. The rotation around the directional axis of the camera 28 can be determined by matching the reconstructed shape with the camera image shape manually or automatically.

The automatic method uses a best-fit algorithm where the look-at vector is fixed, while allowing a search over the rotation around the look-at vector. This means that the up-vector can be determined in a localized manner. The manual method allows the user to rotate the reconstructed shape around the look-at vector manually, for instance by pressing on the edge of the display field of the camera 28.

The afore-mentioned overlaying of the reconstructed shape onto the generated data, in particular the representation of the reconstructed shape using the reference frame of the generated image data, enables to determine a correlation between the position and/or orientation of the interventional device 14 and/or the optical fiber 13 in the reconstructed shape on one hand and the position and/or orientation of the tablet computer 26, 26' on the other hand. Without loss of generality, this determination is called "shape-to-tablet registration".

Preferably, one or more instruments may be physically connected to the interventional device 14, wherein the instruments may be tracked via shape sensing using the apparatus 26, 26'. In particular, the position and/or orientation of the instruments may be obtained, for instance using the optical camera 28 which generates a camera image for the instruments. The result of such a tracking can be used to detect a relation between the instruments and the interventional device 14. For instance, the correlation between the shape of the instruments and that of the interventional device 14 may be determined while both shapes are preferably represented using the reference frame of the camera, its display field and/or the camera image. Without loss of generality, the afore-mentioned determination of a relation between the two shapes is called "shape-to-shape registration".

Preferably, the tablet computer 26, 26' is configured to receive live data feed of the one or more instruments physically connected to the interventional device 14. The unit 23 of the tablet computer 26, 26' is preferably configured to represent the reconstructed shape of the interventional device 14 and/or the optical fiber 13 in a reference frame of the live data feed of the instruments. In particular, the unit 23 is configured to determine the data source or origin of the afore-mentioned live data feed. Further, the unit 23 may use the data source of the live data feed as an input parameter, for instance in the user preferences, for selecting the reference frame when overlaying the reconstructed shape onto the live data feed of the instruments.

The camera 28 is preferably configured to generate a camera image for one or more objects captured in the viewing field of the camera 28, in order to track these objects by determining their position and/or orientation with respect to the camera 28 based on the camera image. This can be done for instance by image detection, e.g. by detecting one or more facial features of a patient in the live camera feed, or by marker detection, e.g. by putting markers at one or more parts of a patient or an instrument in the live camera feed. In this way, one can correlate the position and/or orientation of the tablet computer 26, 26' with the position and/or orientation of the tracked objects. Without loss of generality, the determination of such a correlation is called a "tablet-to-world registration". Preferably, the position and/or orientation of the interventional device according to the reconstructed shape and/or the camera image shape may be correlated with the position and/or orientation of the tracked objects.

Preferably, the tablet computer 26, 26' is attached to a stationary carrier such as a docking station, or a movable carrier, the stationary and/or movable carrier comprising one or more encoders configured to sense specific parameters such as speed, position and/or orientation of the carrier. The position and/or orientation of the tablet computer 26, 26' can thus be determined with help of the encoder. Further, the determined position and/or orientation of the tablet computer 26, 26' can be expressed with respect to the space and/or objects within the space, for instance using the camera feed or data feed obtained from an external entity. In this way, an alternative tablet-to-world registration is performed.

Preferably, the tablet computer 26, 26' comprises a plurality of cameras 28 arranged at two or more edges 42, 44, 46, 50 of the tablet computer 26, 26'. The cameras 28 are configured to track objects in 3D, thereby tracking the position of the objects with respect to the camera feed, in particular to a reference frame of the camera feed, and/or tracking the position and/or orientation of the tablet computer 26, 26' with respect to the tracked objects and/or the space in which the tracked objects exist. In this way, another alternative tablet-to-world registration is performed.

The interventional device 14 may cooperate with a computer tomography (CT) imaging system, a magnetic resonance (MR) imaging system and/or another imaging system known in the field of medical imaging. Preferably, the tablet computer 26, 26' is configured to perform optical shape sensing for the interventional device 14 cooperating with one or more of the afore-mentioned medical imaging techniques.

Further preferably, the tablet computer 26, 26' further comprises or cooperates with an acoustic-to-electric transducer or sensor, in particular a microphone. The microphone is configured to cooperate with the camera 28, whose image capture surface is arranged on the front side 36 of the housing 30, wherein the display field of the display unit 40 is also arranged on the front side 36. This enables advantageously the user facing the display field to interact with the tablet computer 26, 26' by speaking to the microphone, thus without physical/manual contact between the user and the tablet computer 26, 26'. For instance, the tablet computer 26, 26' may be configured to process voice commands such as "display CT on/off", "place landmark at tip of device" and/or "re-register".

As mentioned above, the present invention enables to correlate the information regarding parameters such as shape, position and/or orientation between two different objects, wherein the determination of such a correlation is a registration between the two objects. For instance, a correlation between object A and object B is established by an A-to-B registration.

Preferably, the tablet computer 26, 26' is configured to construct a scene graph of a plurality of objects in order to acquire a registration between any two of the plurality of objects. The plurality of objects may be captured by the camera 28 of the tablet computer 26, 26', so that the position and/or orientation of the objects can be extracted from the live camera feed of the camera 28, preferably represented using the reference frame of the live camera feed. Alternatively, the tablet computer 26, 26' uses live data feed from external entities to extract the position and/or orientation of the plurality of objects. In this way, the position and/or orientation of one of the objects may be represented in a reference frame of the data feed regarding another object and vice versa.

The tablet computer 26, 26' may be configured to enable one or more inputs of the afore-mentioned registrations, wherein the one or more inputs may be blended or superimposed with each other. For instance, several registrations each between two objects may be "chained-up" to perform a new registration. Preferably, a live camera feed-to-CT image registration, a CT-to-ultrasound feed registration and an ultrasound feed-to-live reconstructed shape registration may be chained-up to enable a live camera-to-live reconstructed shape registration.

Preferably, the tablet computer 26, 26' is configured to use live camera feed generated by the optical camera 28 only for tracking devices, such as the interventional device 14. The orientation on the visualization of the inputs may preferably be set to a user-defined orientation. The user-defined orientation refers to the orientation of viewing angles, from which a superimposition of the reconstructed shape on other data, such as medical data or non-medical data of other modalities, may be viewed by the user. The live camera feed is then used only for tracking devices but not an image feed in itself, which would restrict the viewing angle to the current position of the camera 28 due to the two-dimensionality of the image feed.

Preferably, the tablet computer 26, 26' is configured to process gyroscope data and/or accelerometer data, the gyroscope data and/or accelerated data being generated by a gyroscope and/or accelerometer of the tablet computer 26, 26' or from an external gyroscope and/or an external accelerometer, a position tracking unit/sensor, an orientation tracking unit/sensor, and/or based on the shape sensing. The receiving unit 22 is able to receive the position and/or orientation of the tablet computer 26, 26' determined from the processed data, in particular relative to one or more objects in the environment of the tablet computer 26, 26'. The unit 23 is configured to register the reconstructed shape with the camera data by representing the reconstructed shape in a coordinate system based on the received position and/or orientation of the tablet computer 26, 26', in particular the camera 28.

In this way, a registration similar to the afore-mentioned shape-to-tablet registration is realized, wherein the registration is a "blind registration" which does not utilize the live camera feed generated by the camera 28. The position and/or orientation of the optical fiber 13 and/or the interventional device 14 according to the reconstructed shape is registered with respect to one or more objects captured by the gyroscope, the accelerometer, a position tracking unit/sensor, an orientation tracking unit/sensor, and/or based on the shape sensing. Preferably, the interventional device 14 may be positioned in such a way with respect to the optical camera 28 that the sensing tip of the interventional device 14 appears in a center of the display unit 40, wherein the position and/or orientation of the sensing tip is not adapted or matched to the position and/or orientation contained in the live camera feed.

The afore-mentioned different registration methods can be applied to determine the relative or absolute orientation of the apparatus 26, 26', so that the reconstructed shape can be registered by a representation in a coordinate system of based on the received position and/or orientation of the apparatus 26, 26'. Preferably, the reconstructed shape can be overlaid onto the image data generated by the camera 28.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other

The invention claimed is:

1. A medical system for shape sensing by interacting with a shape sensing element, wherein the shape sensing element is configured to perform a shape sensing measurement of an interventional device, and by interacting with an image data generation unit for generating image data, said medical system comprising:
a shape sensing console in communication with said shape sensing element, said shape sensing console for generating measurement signals of said shape sensing measurement;
a processing unit and a non-transitory storage medium for storing instructions that, when executed by the processing unit, cause the processing unit to:
reconstruct a shape of said shape sensing element based on said generated measurement signals;
determine a position and/or orientation of the image data generation unit relative to a subject in a coordinate system based on the generated image data; and
register said reconstructed shape by representing said reconstructed shape in the coordinate system based on said received position and/or orientation of said image data generation unit; and
a connector unit for connecting said shape sensing console to said shape sensing element, wherein said connector unit is detachably connectable to a housing of said image data generation unit.

2. The medical system as claimed in claim 1, wherein the instructions further cause the processing unit to register said reconstructed shape with said image data generated by said image data generation unit.

3. The medical system as claimed in claim 1, wherein the instructions further cause the processing unit to determine said position and/or orientation from additional data obtained by a different unit, said different unit including an orientation tracker, a position tracker, a gyroscope, an accelerometer, a hinged display, a swivel and/or a pendulum.

4. The medical system as claimed in claim 3, wherein the instructions further cause the processing unit to automatically register said reconstructed shape based on the orientation of said image generation data unit facing said subject.

5. The medical system as claimed in claim 1, wherein the instructions further cause the processing unit to perform a rigid coordinate transformation or a look-at transformation, and/or to determine a correlation function and/or a fit between said reconstructed shape and said generated image data.

6. The medical system as claimed in claim 5, wherein the instructions further cause the processing unit to determine a fit between said reconstructed shape and a shape of said shape sensing element extracted from said generated image data.

7. The medical system as claimed in claim 5, wherein the instructions further cause the processing unit to determine an up-vector semi-automatically and/or using user interaction, wherein the up-vector being a direction of an axis in a cross-section of a body part or a three-dimensional representation of a body part displayed in the image data.

8. A method for shape sensing by interacting with a shape sensing element configured to perform a shape sensing measurement of an interventional device and by interacting with an image data generation unit for generating image data, the method comprising:
generating, by a processing unit, measurement signals of said shape sensing measurement using a shape sensing console connected with the shape sensing element by a connector unit;
reconstructing, by the processing unit, a shape of said shape sensing element based on said generated measurement signals;
determining, by a processing unit, a position and/or orientation of the image data generation unit relative to a subject in a coordinate system based on the generated image data;
registering, by a processing unit, said reconstructed shape with said generated image data by representing said reconstructed shape in the coordinate system based on said received position and/or orientation of said image data generation unit; and
detachably connecting the shape sensing console to a housing of said image generation data unit using the connector unit.

9. An apparatus for shape sensing by interacting with a shape sensing element configured to perform a shape sensing measurement of an interventional device, said apparatus comprising:
a housing;
an image data generation unit arranged on a side of the housing for generating image data; and
a medical system configured to interact with the image data generation unit and the shape sensing element, the medical system comprising:
a shape sensing console in communication with the shape sensing element, the shape sensing console for generating measurement signals of the shape sensing measurement of the interventional device;
a processing unit and a non-transitory storage medium for storing instructions that, when executed by the processing unit, cause the processing unit to:
reconstruct a shape of the shape sensing element based on the generated measurement signals;
determine a position and/or orientation of the image data generation unit relative to a subject in a coordinate system based on the generated image data; and
register the reconstructed shape by representing the reconstructed shape in the coordinate system based on the received position and/or orientation of the image data generation unit; and
a connector unit for connecting said shape sensing console to the shape sensing element, wherein the connector unit is detachably connectable to the housing.

10. The apparatus as claimed in claim 9, wherein said apparatus comprises a mobile apparatus.

11. The apparatus as claimed in claim 9, wherein said image data generation unit is configured to generate real-time image data.

12. The apparatus as claimed in claim 9, wherein said image data generation unit comprises an optical camera, an ultrasonic camera and/or a thermal camera.

13. The apparatus as claimed in claim 9, wherein said image data generation unit comprises a plurality of cameras arranged surrounding a plurality of edges of said housing of said apparatus.

14. The apparatus as claimed in claim 9, further comprising a display unit for displaying a content of said image data generated by said image data generation unit and/or displaying said registered reconstructed shape.

\* \* \* \* \*